United States Patent
Han et al.

(10) Patent No.: US 9,546,905 B1
(45) Date of Patent: Jan. 17, 2017

(54) MID-INFRARED SCANNING SYSTEM THAT DIFFERENTIATES BETWEEN SPECULAR AND DIFFUSE SCATTERING

(71) Applicant: Agilent Technologies, Inc., Loveland, CO (US)

(72) Inventors: Yang Han, Sunnyvale, CA (US); Miao Zhu, San Jose, CA (US); Adam Kleczewski, San Francisco, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 87 days.

(21) Appl. No.: 14/683,841

(22) Filed: Apr. 10, 2015

(51) Int. Cl.
*G01J 3/42* (2006.01)
*G01J 3/02* (2006.01)

(52) U.S. Cl.
CPC ............... *G01J 3/42* (2013.01); *G01J 3/0224* (2013.01); *G01J 2003/425* (2013.01)

(58) Field of Classification Search
CPC ....... G01J 3/42; G01J 3/0224; G01J 2003/425
See application file for complete search history.

(56) References Cited

U.S. PATENT DOCUMENTS

| | | | |
|---|---|---|---|
| 5,247,176 A | 9/1993 | Goldstein | |
| 6,310,345 B1* | 10/2001 | Pittman | G01J 4/00 250/330 |
| 6,618,145 B1 | 9/2003 | Goldstein | |
| 6,853,926 B2 | 2/2005 | Alfano | |
| 7,038,208 B2 | 5/2006 | Alfano | |
| 7,298,480 B2 | 11/2007 | Garcia-Caurel et al. | |
| 7,298,492 B2* | 11/2007 | Tixier | G01B 11/0641 356/487 |
| 9,279,770 B2* | 3/2016 | Mossoba | C12Q 1/6816 |
| 2007/0078348 A1* | 4/2007 | Holman | A61B 5/0075 600/473 |
| 2007/0273865 A1* | 11/2007 | Niitsu | G01L 1/241 356/33 |
| 2008/0304047 A1* | 12/2008 | Lee | G01J 3/433 356/51 |
| 2010/0051808 A1* | 3/2010 | Zeman | A61B 5/489 250/330 |

(Continued)

OTHER PUBLICATIONS

Han, P.Y., Time-domain Transillumination of Biological Tissues with Terahertz Pulses, Optics Letters, Optical Society of America, vol. 24, No. 4, Feb. 15, 2000.

*Primary Examiner* — Marcus Taningco (57) ABSTRACT

A method and apparatus for measuring diffuse and specularly reflected light from a sample to provide a reflection spectrum as a function of wavelength and as a function of position on a sample is disclosed. The apparatus includes a MIR light source that generates an illumination beam of linearly polarized light. An illumination system illuminates a location on a specimen with part of the illumination beam. A linear polarization filter characterized by a polarization axis that defines a direction of polarization of linearly polarized light that is reflected by the linear polarization filter, a first detector that measures an intensity of light leaving the linear polarization filter and a light collection system collects light reflected from the location on the specimen and directs that light to the linear polarization filter. A controller measures an output from the first detector for each of a plurality of different polarization axis positions.

20 Claims, 7 Drawing Sheets

(56) References Cited

U.S. PATENT DOCUMENTS

| | | | | |
|---|---|---|---|---|
| 2012/0019835 A1* | 1/2012 | Nakao | ............... | G01N 21/8806 |
| | | | | 356/600 |
| 2013/0002839 A1* | 1/2013 | Pennisi | .............. | G06K 9/00281 |
| | | | | 348/58 |
| 2015/0276864 A1* | 10/2015 | Yurt | .................. | G01N 21/1717 |
| | | | | 324/754.23 |
| 2016/0109630 A1* | 4/2016 | Ichihashi | ............... | C09K 19/54 |
| | | | | 250/338.1 |

* cited by examiner

MID-INFRARED SCANNING SYSTEM THAT DIFFERENTIATES BETWEEN SPECULAR AND DIFFUSE SCATTERING

BACKGROUND

Quantum cascade lasers provide a tunable mid-infrared (MIR) light source that can be used for spectroscopic measurements and images. Many chemical components of interest have molecular vibrations that are excited in the MIR region of the optical spectrum, which spans wavelengths between 5 to 25 microns. Hence, measuring the absorption of MIR light at various locations on a sample can provide useful information about the chemistry of the sample as a function of position on the sample.

SUMMARY

The present invention includes a method and apparatus for measuring diffuse and specularly reflected light from a sample to provide a reflection spectrum as a function of wavelength and as a function of position on a sample. The apparatus includes a MIR light source that generates an illumination beam of linearly polarized light and an illumination system that illuminates a location on a specimen with part of the illumination beam. The apparatus also includes a linear polarization filter characterized by a polarization axis that defines a direction of polarization of linearly polarized light that is reflected by the linear polarization filter, a first detector that measures an intensity of light leaving the linear polarization filter and a light collection system that collects light reflected from the location on the specimen and directs that light to the linear polarization filter. A controller measures an output from the first detector for each of a plurality of different polarization axis positions.

In one aspect of the invention, the beam of linearly polarized light is characterized by a source polarization direction, and the controller causes the source polarization direction to maintain a fixed relationship with respect to the polarization axis positions. In one embodiment, the polarization axis and the source polarization direction are maintained such that light with the polarization direction would pass through the linear polarization filter. In another embodiment the polarization axis and the source polarization direction are maintained such that light with the polarization direction would be blocked by the linear polarization filter.

In another aspect, the controller measures a minimum of five different detector outputs corresponding to five different polarization axes.

In another aspect, the apparatus also includes a sample stage that positions the specimen such that the location corresponds to a plurality of different locations on the specimen.

In another aspect, the linear polarization filter includes a polarization dependent beam splitter that splits light incident thereon into first and second analyzer beams, and the apparatus further includes a second detector, the first detector measuring an intensity of light in the first beam and second detector measuring an intensity of light in the second beam.

In a still further aspect of the invention, the MIR light source is frequency modulated. In one embodiment, the polarization axis is continuously rotated at a rotation frequency, and the controller measures an average intensity from the first detector and an amplitude as a function of a frequency that depends on the rotation frequency. In another embodiment, the controller determines an intensity of diffusely reflected light and an intensity of specularly reflected light from the average intensity and the amplitude.

In another aspect of the invention, the controller determines an intensity of light corresponding to the intensity of diffusely reflected light from the location and the intensity of specularly reflected light having one polarization from the measured output from the first detector.

In a still further aspect, the illumination light beam is characterized by a wavelength, and the controller causes the MIR light source to output light of a second wavelength. The controller measures the output of the first detector for each of the polarization axis positions for the second wavelength.

In another aspect of the invention, the controller varies the polarization axis by rotating the linear polarization filter about an axis defined in relation to the location.

In another aspect of the invention, the controller varies the polarization axis by rotating the specimen about an axis through the location.

In another aspect, the illumination beam is characterized by an illumination polarization direction, and the controller varies the polarization axis position by varying the illumination polarization direction.

In a still further aspect of the invention, the apparatus includes a focal plane array of detectors, the light collection system imaging light from different locations on the specimen to different detectors in the focal plane array. The first detector is one of the focal plane array of detectors.

In a method according to the present invention, the method includes a one wavelength method. The one wavelength method includes illuminating the sample with a beam of linearly polarized light characterized by a measurement wavelength, and a source polarization direction, and filtering light reflected by the sample with a linear polarization filter characterized by a polarization axis that defines a direction of polarization of linearly polarized light that is reflected by the linear polarization filter. The intensity of light leaving the linear polarization filter for each of a plurality of different polarization axis positions is measured, and an intensity of diffusely reflected light from the measured intensities is determined.

In one aspect of the one wavelength method, an intensity of specularly reflected light is also determined from the measured intensities.

In another aspect of the one wavelength method, the source polarization direction is maintained in a fixed relationship with the polarization axis positions.

In another aspect of the method, the one wavelength method is repeated for a plurality of different measurement wavelengths.

DETAILED DESCRIPTION

There are two types of systems for generating images in the MIR. The first type of system for generating images in the MIR can be viewed as a conventional microscope with a MIR light source and an optical system that images the illuminated sample onto an array of MIR detectors. A MIR light source based on a quantum cascade laser provides a tunable MIR light source. There are several problems with such imaging systems.

First, the laser light is spread over the entire field being imaged, which leads to a low local illumination intensity at each point on the specimen. In systems in which the quantum cascade laser is pulsed, the average duty cycle of the light source is small, and a large number of pulses must be integrated on the imaging array. The imaging array cannot be turned on and off in synchrony with the pulses. Hence, during the periods between pulses, the imaging array accumulates noise which lowers the signal-to-noise ratio. To overcome the noise, longer exposure times are required, which increases the time to form an image. In some applications, imaging time is crucial, as the sample is changing chemically or spatially over a time span that is small compared to the image acquisition time in such systems.

Second, if the desired image has many more pixels than the size of the imaging array, a plurality of sub-images must be "stitched" together to form the final image. This process adds artifacts to the final image and further increases the time needed to generate an image.

Third, interference artifacts detract from the images. The light from a quantum cascade laser is coherent. As a result, light that is reflected from adjacent areas on the sample interferes, which leads to speckling in the image that obscures details of interest.

Fourth, zooming in or out to change the resolution of the image requires a plurality of MIR imaging objective lenses. To avoid stitching several images together, the field of view of the microscope can be increased by changing the magnification of the MIR imaging optics. This requires that different objective lenses be utilized. The additional objective lenses and the need to calibrate the imaging array for each objective lens increases the cost and complexity of the system.

Figure 1:
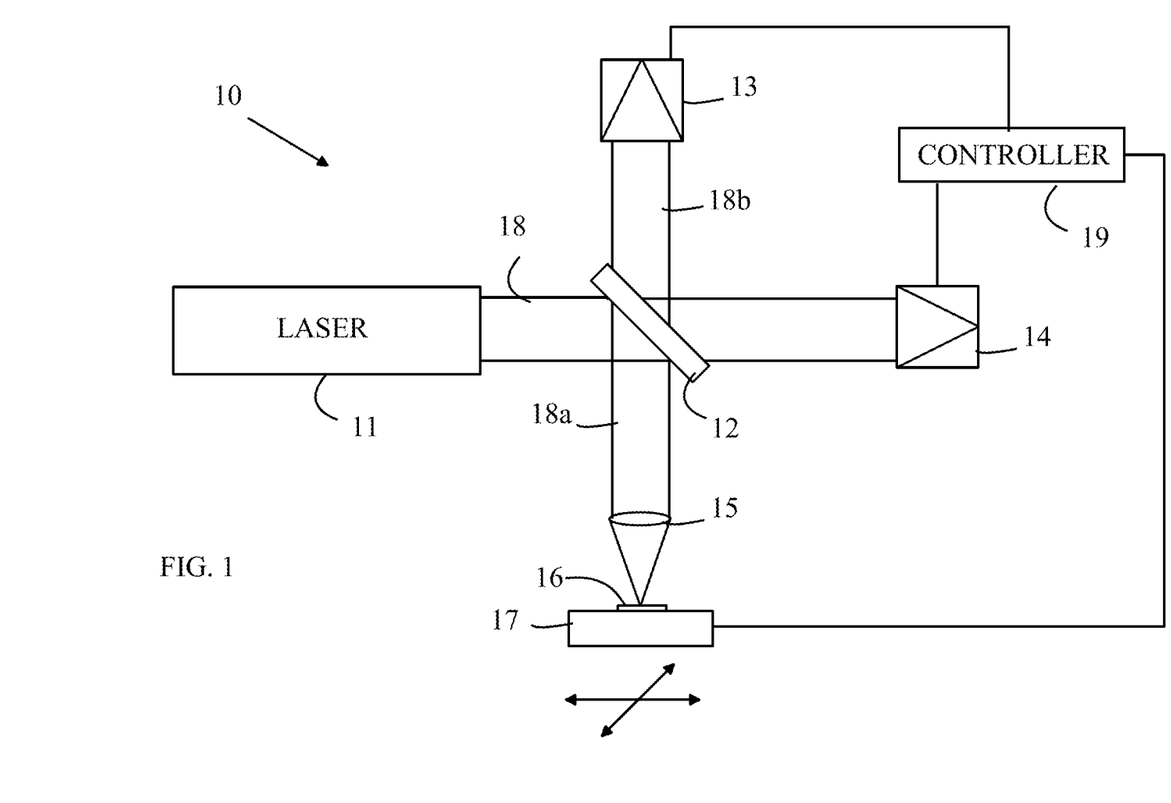
FIG. 1 illustrates one embodiment of a MIR imaging system of the type discussed in this patent application.

A second type of imaging system that substantially reduces these problems is taught in co-pending U.S. patent application Ser. No. 14/599,493 filed Sep. 29, 2014. Refer now to FIG. 1 which illustrates one embodiment of a MIR imaging system of the type discussed in this patent application. Imaging system 10 includes a quantum cascade laser 11 that generates a collimated light beam 18 having a narrow band of wavelengths in the MIR. In one aspect of the invention, laser 11 is a quantum cascade laser having a tunable wavelength that is under the control of a controller 19. Collimated light beam 18 is split into two beams by a partially reflecting mirror 12. Light beam 18a is directed to a lens 15 that focuses that beam onto a specimen 16 that is mounted on xy-stage 17 that can position specimen 16 relative to the focal point of lens 15. Light that is reflected back from specimen 16 is collimated into a second beam that has a diameter determined by the aperture of lens 15 and returns to partially reflecting mirror 12 along the same path as light beam 18a. While the first and second beams are shown as having the same cross-section in FIG. 1, it is to be understood that the second beam could have a different cross-section than the first beam. A portion of the second beam is transmitted through partially reflecting mirror 12 and impinges on a first light detector 13 as shown at 18b. Light detector 13 generates a signal related to the intensity of light in beam 18b. Controller 19 computes an image as a function of position on specimen 16 by moving specimen 16 relative to the focal point of lens 15 using xy-stage 17.

Controller 19 also monitors the beam intensity of the light in collimated light beam 18 using a second light detector 14 that receives a portion of the light generated by quantum cascade laser 11 through partially reflecting mirror 12. Quantum cascade laser 11 is typically a pulsed source. The intensity of light from pulse to pulse can vary significantly, and hence, the pixels of the image are corrected for the variation in intensity by dividing the intensity measured by light detector 13 by the intensity measured by light detector 14. In addition, since the light intensity from quantum cascade laser 11 is zero between pulses, controller 19 only sums the ratio of intensities from light detectors 13 and 14 during those times at which the output of light detector 14 is greater than some predetermined threshold. This aspect of the present invention improves the signal-to-noise ratio of the resultant image, since measurements between pulses contribute only noise, which is removed by not using measurements between pulses.

As noted above, when a coherent light source is used to illuminate the entire specimen, interference between light reflected from different portions of the specimen leads to image artifacts that result from the interference of the coherent light leaving different parts of the specimen. If two points that are illuminated are sufficiently close that light from each point is received at the detector, the light from the two points is coherently combined leading to intensity variations that cannot be easily distinguished from variations in the reflected light intensities. Hence, when the entire area of interest on the specimen is illuminated, light that is reflected from adjacent regions on the specimen can reach the same pixel on the imaging array, leading to interference artifacts. The present invention avoids such artifacts by using an illumination system in which light from only one point on the specimen is received by light detector 13.

Both types of imaging systems can benefit from measuring the absorption of the incident light as a function of wavelength to create an absorption spectrum at each point in the image. In absorption spectroscopy, the sample is illuminated with light and the amount of light that is reflected from the sample is measured. The process is repeated for a number of wavelengths of the light to generate a spectrum consisting of the intensity of the reflected light as a function of wavelength. The fraction of the incoming light that is reflected from the sample is related to the intensity of the light that was absorbed by the sample. Absorption spectra can be used to identify the chemical compounds in the sample. Hence, an image of a sample in which each pixel of the image includes an absorption or reflection spectrum as a function of wavelength is useful in visualizing the distribution of different chemical compounds in the sample.

The light that is reflected from a specimen depends on the nature of the surface of the specimen. In general, the reflected light is a mixture of specular reflected light from flat surfaces such as the facets of crystals in the sample and diffuse reflected light reflected from rough surfaces or powders. The spectra generated by specularly reflected light differ from those generated by diffusely reflected light. Since many specimens of interest generate a compound spectrum with an unknown ratio of the two types of reflections, interpreting the images in terms of the chemical composition of a sample as a function of position on the sample presents significant challenges. These challenges can be significantly reduced if the contribution of each type of reflection to the measured spectrum at each point in the specimen can be separated.

The present invention is based on the observation that polarized light that is undergoing specular reflection remains polarized. In contrast, diffusely reflected polarized light is depolarized. Hence, the diffusely reflected light can be selectively measured with the aid of a linear polarization filter. If the incident laser light is linearly polarized, the specularly reflected light will be linearly or elliptically polarized. The elliptically polarized light can be characterized by two linear polarizations that are orthogonal to one another as measured on a coordinate system that is fixed relative to the specimen. A linear polarization filter blocks linearly polarized light that has a direction of polarization that is orthogonal to a polarization axis defined on the filter. If a light beam is linearly polarized with a direction that is parallel to that axis, all of the light passes through the filter. If the light beam is linearly polarized along a direction that is orthogonal to that axis, all of the light is blocked. In general, if the light is linearly polarized along an axis that is at an angle of θ with respect to the polarization axis, the light can be viewed as having a component that is parallel to the polarizer axis and one that is orthogonal to the polarizer axis. The parallel component passes through the filter and the orthogonal component is blocked by the filter. Hence, for an elliptically polarized beam having linearly polarized components $I_s$ and $I_d$ relative to the coordinate system on the sample, part of the light in each component will pass through the filter. The amount of light will depend on the angle between the polarization axis on the filter and the polarization of each linearly polarized component. By making a number of measurements at different relative angles between the polarization axis and the coordinate system on the sample, different combinations of the diffuse and specular light intensity, $I_d$, $I_s$ and $I_p$ can be measured. These measurements can then be combined to obtain the diffuse and specular components.

Figure 2:
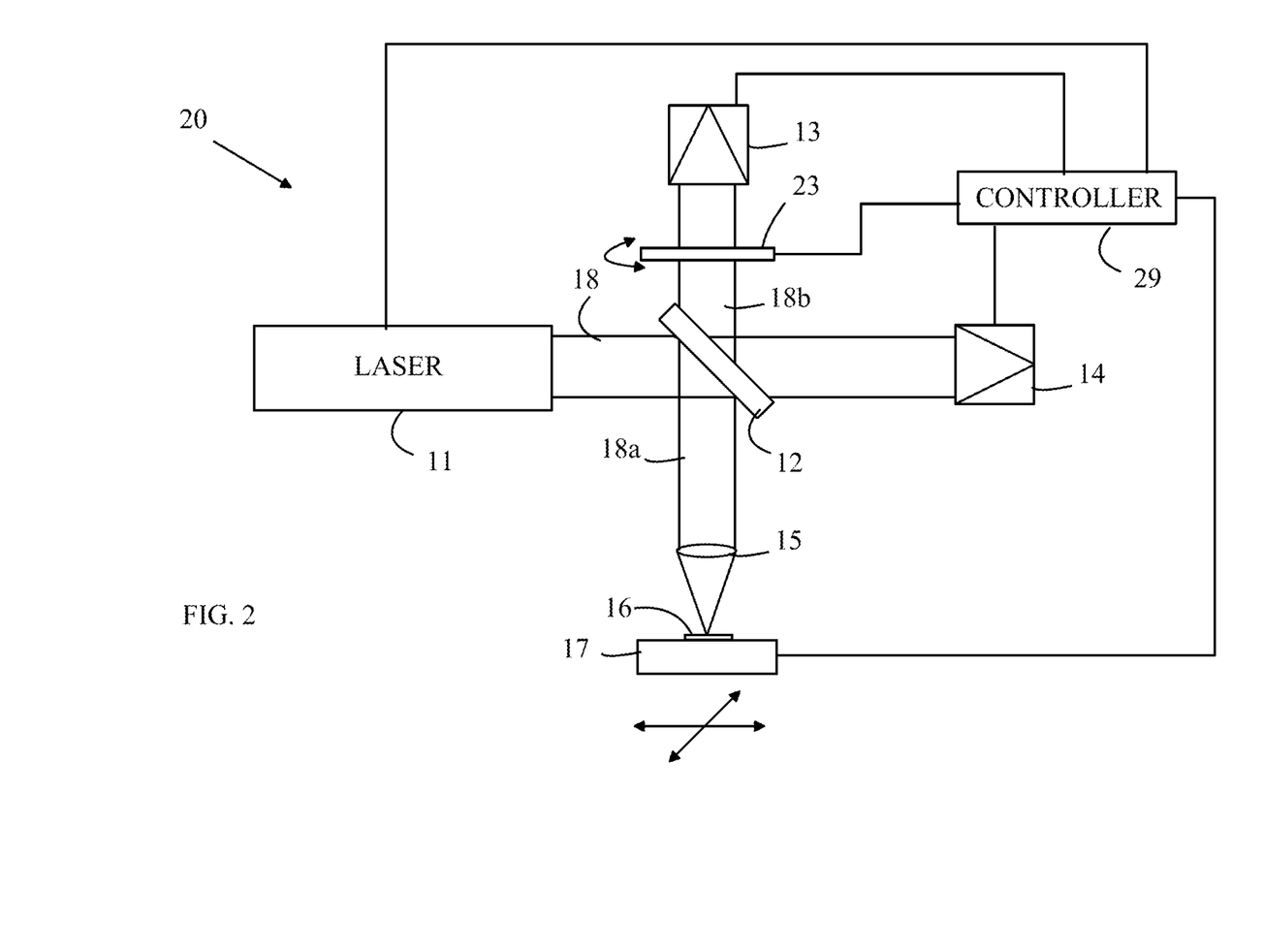
FIG. 2 illustrates one embodiment of a spectrometer according to the present invention.

Refer now to FIG. 2, which illustrates one embodiment of a spectrometer according to the present invention. To simplify the present discussion, those elements of spectrometer 20 that perform functions analogous to those discussed above with respect to imaging system 10 have been given the same numeric designations. Spectrometer 20 utilizes a linear polarization filter 23 which is under the control of controller 29 to separate the specularly reflected light from the diffusely reflected light. Linear polarization filter 23 is rotated through a number of angles in a manner that will be described in more detail below. For each (x,y) coordinate of xy-stage 17 and wavelength of light from quantum cascade laser 11, controller 29 measures the intensity of light reflected back from specimen 16 as a function of the angle of rotation of the polarization axis of linear polarization filter 23. In one aspect of the invention, the intensity measured by light detector 13 is normalized to the output of light detector 14 to correct for variations in the intensity of light generated by quantum cascade laser 11. The measured values as a function of angle of rotation of the polarization axis are then fitted to a function to determine the intensities of the specularly reflected light and the diffusely reflected light. The details of this fitting process will be discussed in detail below. As will be explained in more detail below, the measured intensity as a function of polarization filter angle depends on six factors that include the intensity of the diffusely reflected light, $I_d$, and $I_s$ and $I_p$. Hence, for each wavelength and (x,y) position on the specimen, the desired intensities can be obtained using conventional data fitting techniques applied to at least six measurements of the intensity of light from the detector as a function of the polarization filter angle.

The intensity of light from light detector 13 as a function of the polarization axis angle is given by $$D(\theta) = \frac{I_d}{2} + I_s\cos^2(\theta - \theta_0) + I_p\sin^2(\theta - \theta_0) + \quad (1)$$
$$2\sqrt{I_s I_p} \cos(\varphi_1 - \varphi_2)\sin(\theta - \theta_0)\cos(\theta - \theta_0) +$$
$$\sqrt{2I_s I_d} \cos\varphi_1\cos(\theta - \theta_0) + \sqrt{2I_p I_d} \cos\varphi_2\sin(\theta - \theta_0)$$

where, $\theta_0$ is the angle that maximizes the s-component of the specularly reflected light, and $\varphi_1$ and $\varphi_2$ are phase differences between the specular components and diffuse reflection. Given a minimum of six measurements of D(θ) for different θ values, the parameters can be determined by finding the parameters that minimize an appropriate optimization function such as the least squared difference function:

$$\sum_i (D_i - D(\theta_i))^2 \quad (2)$$

Figure 3:
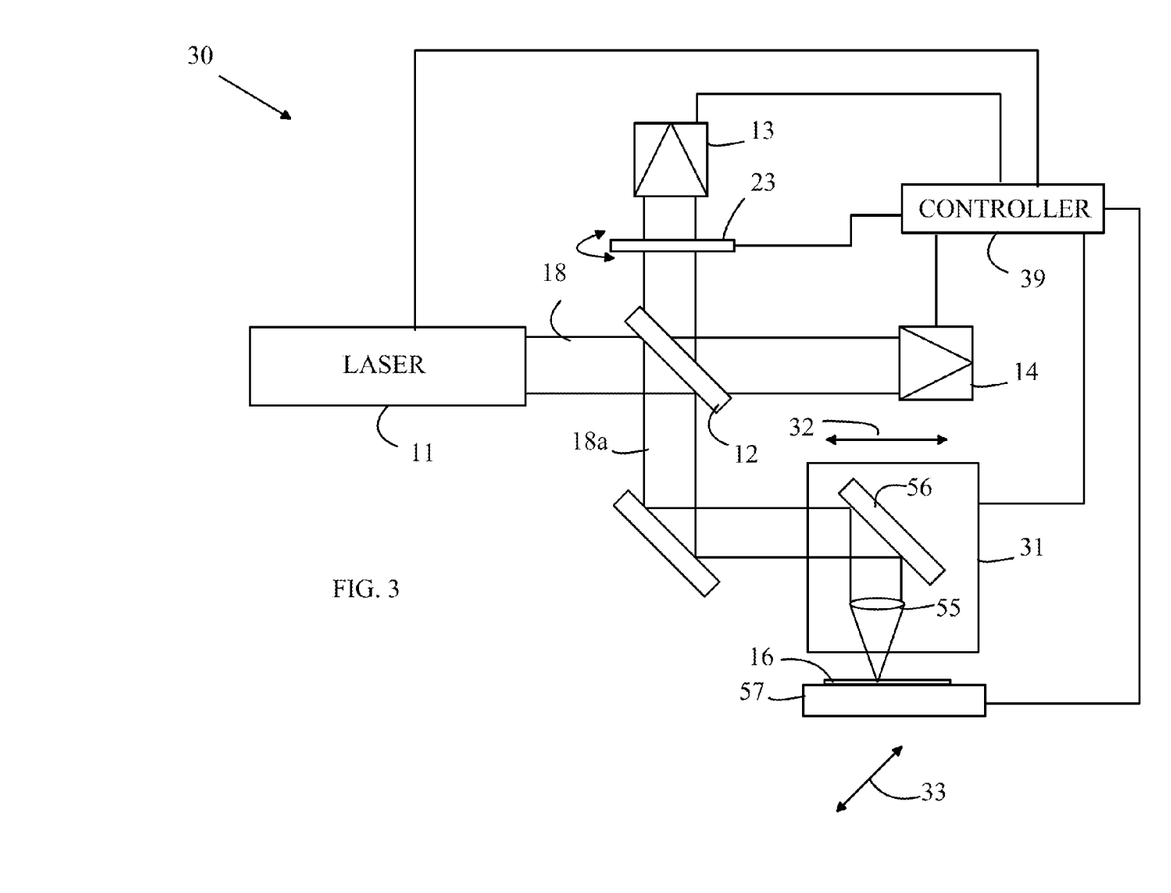
FIG. 3 illustrates another embodiment of an imaging system according to the present invention.

The polarization data must be acquired for each point on the specimen and each wavelength. The order in which the data is taken will depend on a number of factors. If the speed of rotation of the polarization filter is the factor limiting the data acquisition rate, a system in which the polarization is held constant while the stage scans in the x direction has some advantages. In the above described embodiments, the stage moves the sample in two dimensions. However, the stage has a significant mass, and hence, the speed at which the sample is imaged is limited by the motion of the stage. In embodiments in which rapid imaging time is important, embodiments in which the specimen is scanned in one direction by moving lens 15 are preferred. Refer now to FIG. 3, which illustrates another embodiment of an imaging system according to the present invention. In imaging system 30, the stage assembly is divided into two components. Component 31 includes focusing lens 55 and is moveable in a direction shown at 32 such that a single line of the image is generated with each pass of component 31. Since focusing lens 55 and mirror 56 have a mass that is small compared to component 57, component 31 can be moved with much greater speed. In one embodiment, component 31 is mounted on a rail and moved in a manner analogous to a print head on an inkjet printer. The second component of the stage assembly is shown at 57. Component 57 includes the mounting mechanism for the specimen being scanned and moves in a direction 33 that is orthogonal to direction 32. Since component 57 only needs to move once per scan line, the slower speed of motion associated with the more massive component 57 is acceptable. Controller 39 controls the wavelength of quantum cascade laser 11, the axis of linear polarization filter 23, and the position of component 31.

In the arrangement shown in FIG. 3, a line in the x-direction is repetitively scanned while changing the angle of linear polarization filter 23 between scans. If the mechanism that indexes linear polarization filter 23 to the next angle is fast enough to make the change while component 31 reverses direction, then the increase in scanning time required to acquire the desired data is approximately a factor of two. The laser frequency can be changed at the end of each set of x-scans or the entire imaging process can be repeated at the next laser frequency after the data for the image at the current laser frequency is acquired.

Figure 4A:
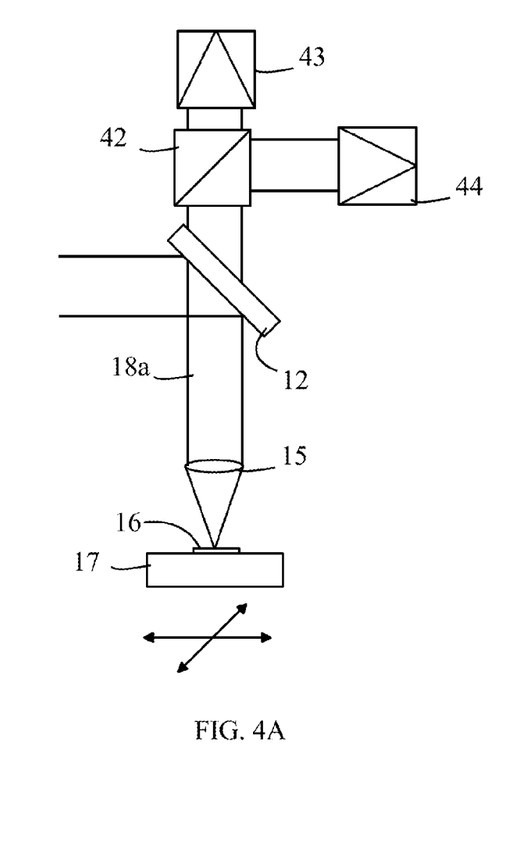
FIGS. 4A and 4B illustrate two embodiments of an optical system for use in the present invention that utilize a polarization beam splitter and two detectors.
Figure 4B:
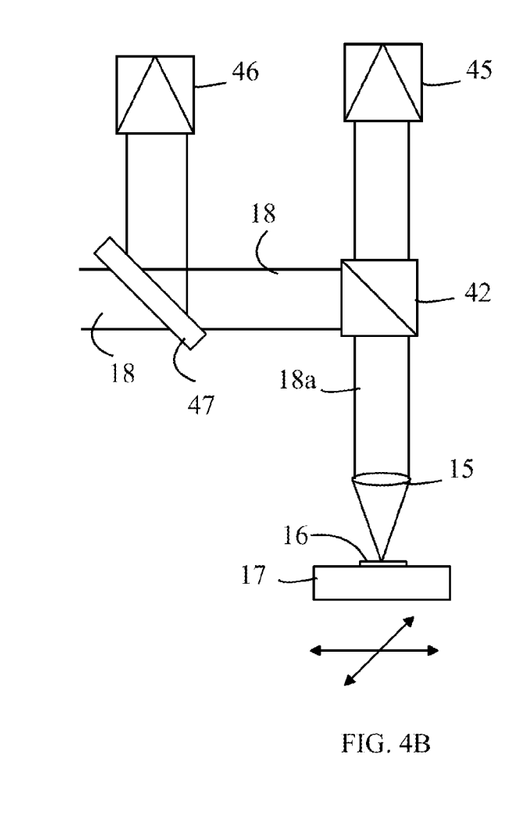

In the above-described embodiments, the light returning from the specimen was filtered through a polarization filter and detected by a single detector. Such an arrangement wastes signal in that the light that does not reach the detector is not utilized. This situation can be improved by replacing the linear polarization filter 23 with a rotating polarization dependent beam splitter and using a second detector to detect the reflected light of the orthogonal polarization. Refer now to FIGS. 4A and 4B which illustrate two embodiments of an optical system for use in the present invention that utilize a polarization beam splitter and two detectors. To simplify the discussion, those elements of the optical systems that perform operations analogous to elements shown in FIG. 2 have been given the same numeric designations. In addition, the detector that measures the intensity of the laser light, i.e., light detector 14 or its equivalent, has been omitted from the figures.

Refer first to FIG. 4A. In this scheme, the light from the specimen is input to a polarization dependent beam splitter 42 which separates the light into a first beam that is detected by detector 43 and a second beam that is detected by detector 44. If the angle of the polarization dependent beam splitter 42 is set such that the equivalent polarization axis for the light measured by detector 43 is at angle θ, then the light measured by detector 44 is equivalent to a measurement at a polarization axis at angle θ+90°. Hence, to provide the six required measurements, at least three different rotations of the polarization dependent beam splitter relative to the coordinate system on the sample must be made.

Refer now to FIG. 4B. In this scheme, the intensity of diffusely reflected light that reaches the detectors is increased relative to the other embodiments discussed above. In the scheme shown in FIG. 4B, polarization dependent beam splitter 42 serves the function of partially reflecting mirror 12 in the other embodiments. Polarization dependent beam splitter 42 is arranged such that all of the laser light that reaches polarization dependent beam splitter 42 is reflected to the sample. The returning light is split by polarization dependent beam splitter 42 into a first beam that is measured by detector 45 and a second beam that is measured by detector 46 after half of its intensity is lost by being reflected from partially reflected mirror 47. If the intensity of diffused light leaving the sample is $I_d$, $0.5I_d$ reaches detector 45 and $0.25I_d$ reaches detector 46. In contrast, the arrangement shown in FIG. 4A results in $0.25I_d$ being received by each detector. To provide measurements at different θ values, the sample must be rotated rather than the polarization dependent beam splitter in the arrangement shown in FIG. 4B.

In the schemes shown in FIGS. 2 and 4A, the different polarization filter angles are obtained by rotating the polarization filter to alter the polarization of the light from the sample that reaches the detector or detectors. The polarization of the light leaving the sample is a function of the polarization of the incident laser light. Hence, embodiments in which the direction of polarization of the incident laser light is altered can also be utilized. For example, the orientation of the laser module can be altered.

The above multi-detector embodiments reduce the number of polarization filter positions that must be utilized in arriving at the number of measurements needed to solve for the intensities of interest. However, the physical motion of the polarization filter or the laser is still required. Embodiments in which beam splitters and multiple detectors are used to collect all of the necessary measurements without physically moving the polarization filter can also be constructed based on the embodiment shown in FIG. 4A.

Figure 5:
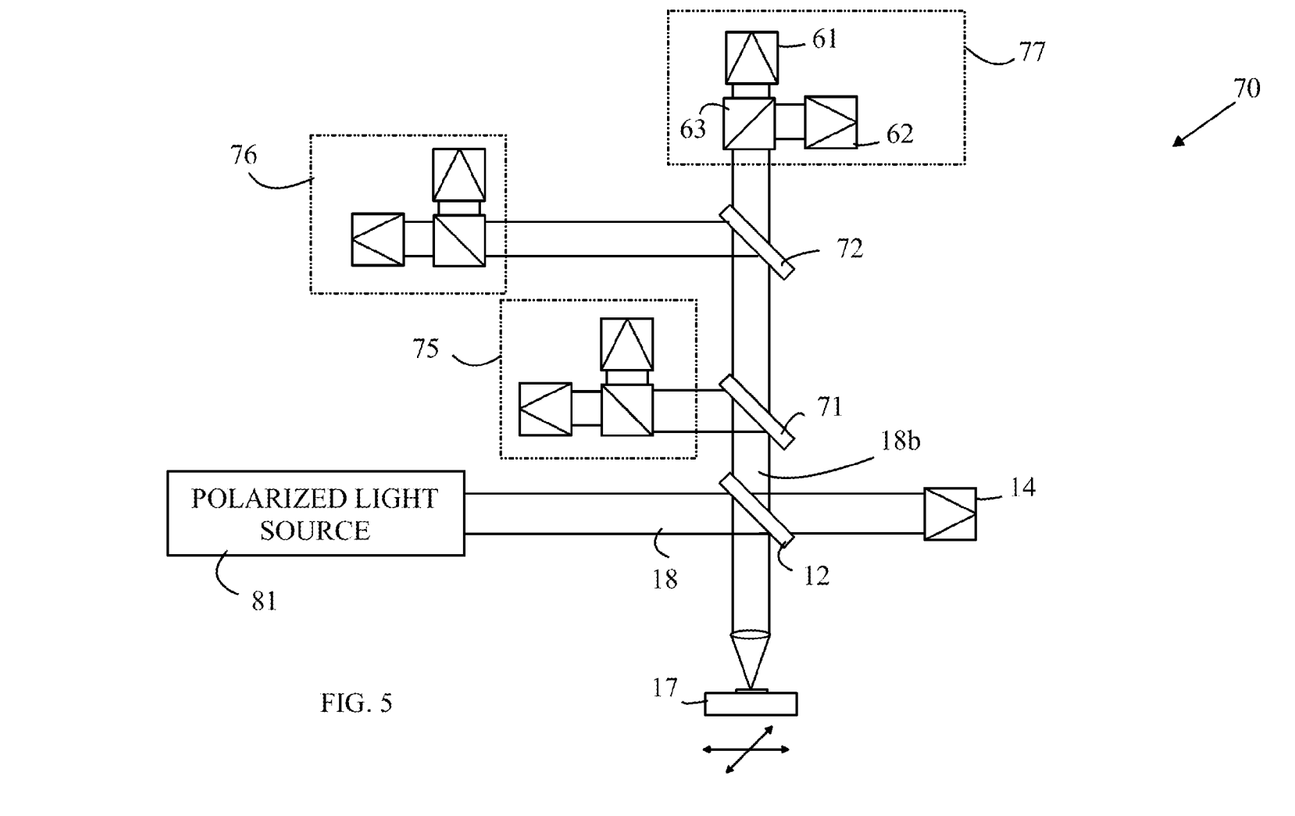
FIG. 5 illustrates another embodiment of an imaging spectrometer according to the present invention.

Refer now to FIG. 5, which illustrates another embodiment of an imaging spectrometer according to the present invention. To simplify the discussion, those elements of spectrometer 70 that perform functions analogous to elements in spectrometer 20 have been given the same numeric designations and will not be discussed in more detail here. Also, the controller that is connected to the various detectors, collimated light beam 18 and xy-stage 17 have been omitted. In spectrometer 70, light leaving the specimen along beam 18b is split into three beams of equal intensity by partially reflecting mirrors 71 and 72. Partially reflecting mirror 71 reflects one-third of the light to analyzer 75 and two-thirds of the light to partially reflecting mirror 72. Partially reflecting mirror 72 splits the light input thereto into two beams of equal intensity. Each light beam is processed by a separate analyzer; the analyzers are shown at 75-77. Each analyzer has a polarization dependent beam splitter and two detectors. Exemplary detectors are shown at 61 and 62 in analyzer 77. The polarization dependent beam splitter in analyzer 77 is shown at 63. Each analyzer operates in a manner analogous to that shown in FIG. 4A. The beam splitters in the three analyzers are set such that the set of six measurements provided by the detectors in the analyzers provides the six different polarization axis measurements needed to determine the intensities, $I_d$, $I_s$, and $I_p$ discussed above. It will be clear from the above discussion that embodiments having additional analyzers that provide other polarization axis values could also be constructed. In addition, polarized light source 81 could include a mechanism that generates light of different linear polarizations in response to the controller. In that case, additional polarization values could be measured.

If the detectors shown in FIG. 5 have sufficiently low noise, such an arrangement can provide a mechanism for making multiple polarization angle measurements without requiring that a polarization filter be physically rotated. However, it must be noted that the intensity of the reflected light signal per detector is reduced by the addition of each analyzer. In the arrangement shown in FIG. 5, each detector receives one-twelfth of the diffusely reflected light from the sample. If the detector noise is large compared to that intensity, extracting the desired intensity value presents significant challenges.

The above analysis assumes that the polarization filters are perfect. That is, any component of the polarization at right angles to the polarization axis of the filter is completely blocked by the filter. In practice, some small fraction of this light will pass through the filter. Accordingly, a fraction of the spectrally reflected light could appear as diffusely reflected light. If the pass through fraction is known, the intensity of diffusely reflected light can be corrected once the specularly deflected light intensities are known.

The above described embodiments assume that the laser frequency is constant during the measurement of a single point on the specimen and a single angle of the polarization filter. If the laser frequency is modulated, the line width over which the reflections are measured is increased, and hence, the spectral information is averaged over a small range of wavelengths corresponding to the modulation frequency. Such modulation, however, can provide additional advantages. First, the modulation can reduce the effects of noise in the detectors, since the detectors can include a band pass filter at the modulation frequency which blocks noise at other frequencies. As noted above, noise can be a problem if the intensity of the diffusely reflected light is low.

Second, by averaging the signal over a number of periods of the modulation frequency, the equation for $D(\theta)$ described above can be simplified. If the modulation frequency is sufficiently small, the intensities $I_d$, $I_s$, $I_p$, and $\theta_0$ can be assumed to be constant over the modulation frequency range. Hence, the average of $D(\theta)$ over times that are long compared to the modulation frequency period, is given by $$\overline{D}(\theta) = \frac{I_d}{2} + I_s\cos^2(\theta - \theta_0) + I_p\sin^2(\theta - \theta_0) + \quad (3)$$
$$2\sqrt{I_sI_p}\,Av(\cos(\varphi_1 - \varphi_2))\sin(\theta - \theta_0)\cos(\theta - \theta_0) +$$
$$\sqrt{2I_sI_d}\,Av(\cos\varphi_1)\cos(\theta - \theta_0) + \sqrt{2I_pI_d}\,Av(\cos\varphi_2)\sin(\theta - \theta_0))$$

Here, Av(x) is the average value of x over the modulation frequency range. The modulation of the light source results in a time dependent frequency of the electric field. The phase relation between s- and p-components of specular reflection and diffuse reflection are strongly dependent on the laser frequency. Hence, if the laser is frequency modulated at a frequency such that $$Av(\cos\phi_1) = Av(\cos\phi_2) = 0, \quad (4)$$

and the equation for the measured signal becomes $$\overline{D}(\theta) = \frac{I_d}{2} + I_s\cos^2(\theta - \theta_0) + I_p\sin^2(\theta - \theta_0) + \quad (5)$$
$$2\sqrt{I_sI_p}\,Av(\cos(\varphi_1 - \varphi_2))\sin(\theta - \theta_0)\cos(\theta - \theta_0)$$

Accordingly, there are now only five unknown parameters to be determined from the detector values at the different polarization angles, namely, $I_d$, $I_s$, $I_p$, $\theta_0$, and $Av(\cos(\phi_1-\phi_2))$. In addition to reducing the minimum number of polarization angles that must be measured, this simplification substantially reduces the computational workload of fitting the observed measurements to the unknown parameters. The level of modulation must be sufficient to satisfy Equation (4). In addition, the modulation frequency must be detectable by the detectors.

Equation (5) can be written in the following format:

$$\overline{D}(\theta) = A_0 + A\cos(2\theta - \psi)$$
$$A_0 = 0.5(I_d + I_s + I_p)$$
$$\psi = 2\theta_0 + \delta \quad (6)$$

Here, $$\text{Where } A = \frac{1}{2}\sqrt{(I_S - I_P)^2 + 4I_SI_P\cos^2(\varphi_1 - \varphi_2)} \quad (7)$$

$$\sin\delta = \frac{\sqrt{I_SI_P}\cos(\varphi_1 - \varphi_2)}{A}, \cos\delta = \frac{I_S - I_P}{2A} \quad (8)$$

Consider the case in which the polarization angle constantly changes at an angular rate of $w_p$. Then, Equation (6) becomes $$\overline{D}(\theta) = A_0 + A\cos(4w_pt - \psi)$$
$$A_0 = 0.5(I_d + I_s + I_p)$$
$$\psi = 2\theta_0 + \quad (9)$$

Consider the case in which the output of the detector is averaged over a large number of revolutions of the polarizer. Since the average value of cosine over a large number of cycles is 0 independent of the starting angle, the average detector signal is just $A_0$. It is also clear that $D(\theta) - A_0$ is a cosine function whose amplitude is A and whose intercept is $\psi$. The amplitude can also be determined without performing any curve fitting. In fact, by filtering the output of the detector through a band pass filter centered at a frequency of $4w_p$, the noise in the detection can be reduced. This approach has a significantly lower computation workload than the fitting embodiments discussed above.

The parameters in Equation (9) can be further simplified in a number of cases of interest. If the sample is reasonably flat and the laser beam is perpendicular to the sample at the point of focus, $I_p \ll I_s$. In this case, $A = 0.5I_s$. Hence, the diffuse intensity and the specular intensity can be determined from $A_0$ and A.

If the sample is a dielectric in which the ratio of the imaginary part of the index of refraction to the refractive index is small, then $\phi_1 - \phi_2$ is approximately $\pi$. In this case, $A = 0.5*(I_s + I_p)$. Hence, $I_d$ can be determined from $A_0$ and A. Given $I_d$ and the total intensity of reflected light, the intensity of specularly reflected light can be determined.

In the general case, Equations (6)-(8) cannot solve the $I_s$ and $I_p$ separately because the value of $\theta_0$ cannot be determined by fitting these equations to any number of measurements, since the values of $\psi$ are determined and without a knowledge of $\theta_0$, values of $\delta$ cannot be obtained. This problem can be solved by utilizing embodiments in which the polarization of the incident light is also controlled. In the above-described embodiments, the incident light is linearly polarized with a polarization that remains constant while the polarization filter in front of the detector that views the light reflected from the sample is rotated.

Figure 7:
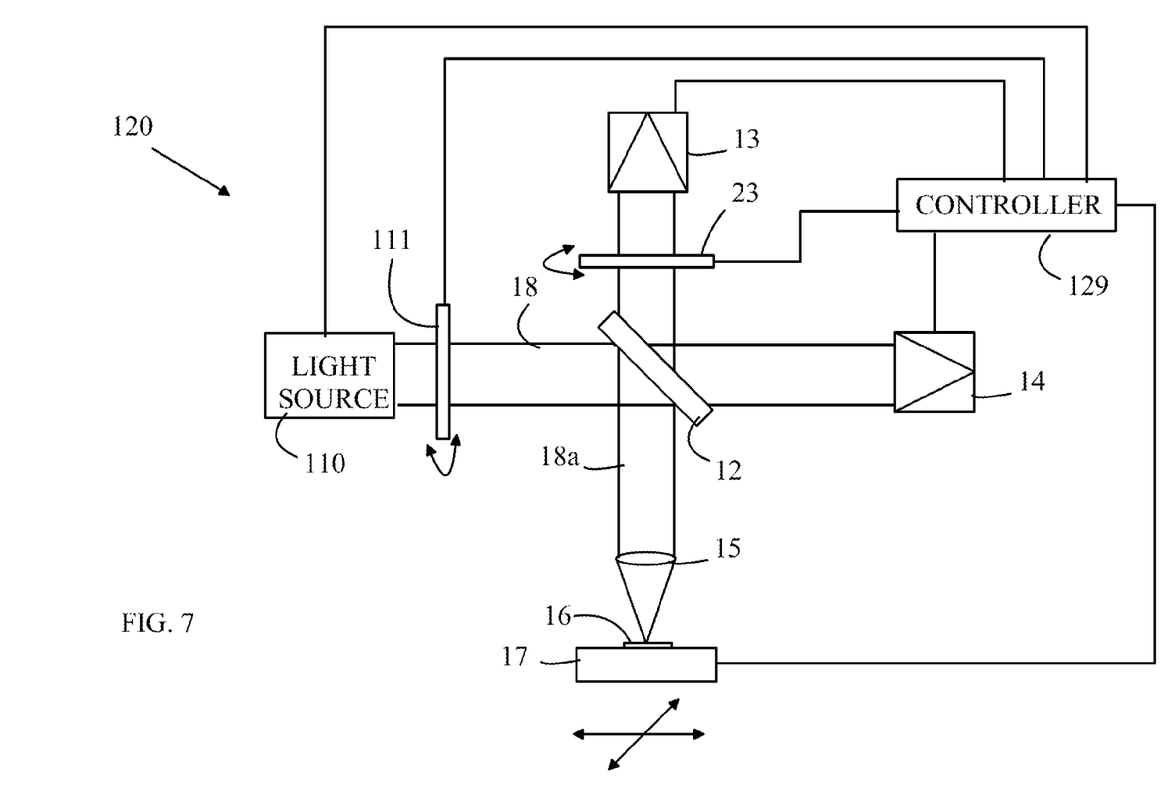
FIG. 7 illustrates another embodiment of an imaging system according to the present invention.

Refer now to FIG. 7, which illustrates another embodiment of an imaging system according to the present invention. Imaging system 120 utilizes a light source in which the light in collimated light beam 18 is linearly polarized with a direction that rotates about the axis of collimated light beam 18 in synchrony with linear polarization filter 23 by controller 129. In the example shown in FIG. 7, the light source consists of an un-polarized light source 110 followed by a rotating polarization filter 111. However, any light source that can generate a linearly polarized beam with a rotating polarization could be utilized. Consider the case in which the polarization of the light in collimated light beam 18 is 90 degrees from the polarization of the light passing through linear polarization filter 23, that is, light of this polarization would be blocked by linear polarization filter 23. In this case, it can be shown that the detector signal is proportional to $$D_1(\theta) = \tfrac{1}{4}(r_s^2 + r_p^2 + 2r_sr_p\cos(\phi_{sp}))\sin^22(\theta - \theta_0) + r_d^2/2 \quad (10)$$

Here, $r_s$ and $r_p$ are the sample's reflection coefficients for the s-component and p-component of the polarized light, respectively. The reflection coefficients are related to the light intensities discussed with respect to other embodiments, by $$I_s = I_0[\cos(\theta_{beam} - \theta_0)]^2 r_s^2$$

$$I_p = I_0[\sin(\theta_{beam} - \theta_0)]^2 r_p^2$$

$$I_d = I_0 r_d^2$$

Here, $\theta_{beam}$ is the angle of polarization of the light from the light source, and $\phi_{sp} = \phi_1 - \phi_2$.

It should be noted that the value of $\theta$ that minimizes $D_1(\theta)$ is $\theta_0 \pm \pi/2$. In addition, the minimum value of $D_1(\theta_0)$ provides the value of $I_d$. This information can be combined with the measurements of $D(\theta)$ discussed above to provide the intensities in the more general case.

Alternatively, a further set of detector measurements, $D_2(\theta)$, can be made with the polarization of collimated light beam 18 being parallel to that accepted by linear polarization filter 23. In this case, the detector signal is proportional to $$D_2(\theta) = \tfrac{1}{4}((r_s^2 + r_p^2 - 2r_s r_p \cos(\phi_{sp})) + r_d^2/2 + \tfrac{1}{4}(r_s^2 + r_p^2 + 2r_s r_p \cos(\phi_{sp}))\cos 2(\theta - \theta_0) + \tfrac{1}{2}(r_s^2 - r_p^2)\cos 2(\theta - \theta_0) \quad (11)$$

The measurements of $D_1(\theta)$ and $D_2(\theta)$ for a number of different $\theta$ values can then be fit to obtain values of the intensities discussed above.

As noted above, the light source in imaging system 120 can be any source that produces a linearly polarized beam of the desired wavelengths in which the polarization vector can be rotated synchronously with that of the polarization filter that processes the light reflected from the sample. Other light sources having this property can be constructed by physically rotating the MIR lasers discussed above. In addition, light sources that used combinations of waveplates and polarizers to rotate the polarization of the linearly polarized light from such a laser could also be utilized.

Figure 6:
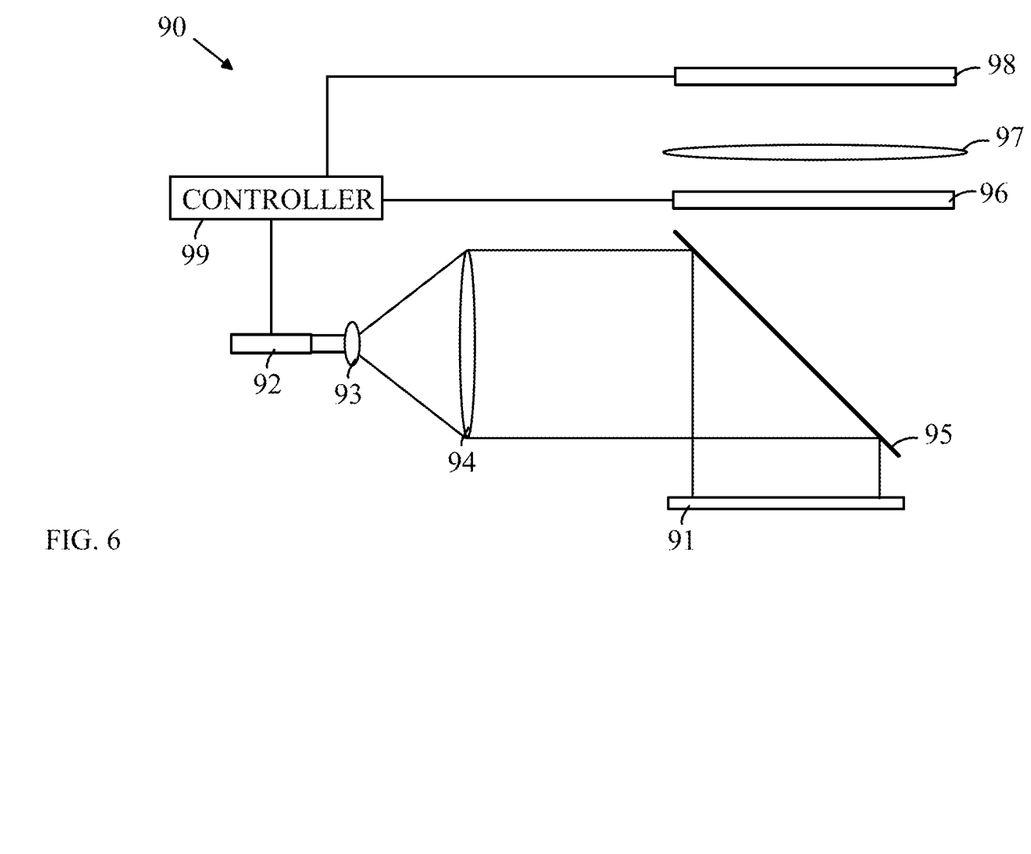
FIG. 6 illustrates another embodiment of a MIR imaging system according to the present invention.

While single point detection imaging systems are preferred, the system of the method of the present invention can be utilized with the first type of imaging system discussed above in which the light from the laser is used to illuminate the entire sample and an array of MIR detectors forms the image of all points in the field of view. Refer now to FIG. 6, which illustrates another embodiment of a MIR imaging system according to the present invention. Imaging system 90 forms images of a specimen 91 at various wavelengths of linearly polarized light source 92 using a focal plane array 98 of MIR detectors. Specimen 91 is illuminated with the aid of lenses 93 and 94 which expand the output of linearly polarized light source 92 to a diameter sufficient to illuminate all of the field of view on specimen 91. The expanded light beam is directed to specimen 91 by partially reflecting mirror 95. Light reflected from specimen 91 that passes through partially reflecting mirror 95 is imaged onto focal plane array 98 by linear polarization filter 97. A rotating linear polarization filter 97 is operated by controller 99 in the same manner as collimated light beam 18 discussed above with respect to FIG. 2. Each detector in focal plane array 98 receives light in a manner described by the equations for $D(\theta)$ discussed above. At each angle of rotation of polarization filter 96, an image is formed. Each pixel in that image is treated as a separate single MIR detector and the $I_s$, $I_p$, and $I_d$ values associated with that pixel are then determined from the separate images taken at different polarization filter settings in a manner analogous to that described above. Hence, for each wavelength, three images can be generated based on the calculated values of $I_s$, $I_p$, and $I_d$. In one aspect, the number of images is reduced to two by combining the images based on $I_s$ and $I_p$ to provide one image based on specular reflection.

In the above described embodiments, it is assumed that the controller in the imaging system determines the values of $I_d$, $I_s$, and $I_p$ from the measured intensity values for the various polarization axis positions. However, embodiments in which the determination of the intensity values in question is determined by another data processing system that receives the measured detector values and polarization axis positions can also be constructed. The solution of the optimization problem discussed above with reference to Equation (3) is well suited to processors having significant parallel processing capability, and hence, if real-time image data is not required, it may be economically advantageous to off load this processing to such processors.

The above-described embodiments of the present invention have been provided to illustrate various aspects of the invention. However, it is to be understood that different aspects of the present invention that are shown in different specific embodiments can be combined to provide other embodiments of the present invention. In addition, various modifications to the present invention will become apparent from the foregoing description and accompanying drawings. Accordingly, the present invention is to be limited solely by the scope of the following claims.

What is claimed is:

1. An apparatus comprising:
   a MIR light source that generates an illumination beam of linearly polarized light;
   an illumination system that illuminates a location on a specimen with part of said illumination beam;
   a linear polarization filter characterized by a polarization axis that defines a direction of polarization of linearly polarized light that is reflected by said linear polarization filter;
   a first detector that measures an intensity of light leaving said linear polarization filter;
   a light collection system that collects light reflected from said location on said specimen and directs that light to said linear polarization filter; and
   a controller that measures an output from said first detector for each of a plurality of different polarization axis positions.

2. The apparatus of claim 1 wherein said illumination beam of linearly polarized light is characterized by a source polarization direction and wherein said controller causes said source polarization direction to maintain a fixed relationship with respect to said polarization axis position.

3. The apparatus of claim 2 wherein said polarization axis and said source polarization direction are maintained such that light with said polarization direction would pass through said linear polarization filter.

4. The apparatus of claim 2 wherein said polarization axis and said source polarization direction are maintained such that light with said polarization direction would be blocked by said linear polarization filter.

5. The apparatus of claim 1 wherein said controller measures a minimum of five different detector outputs corresponding to five different polarization axes.

6. The apparatus of claim 1 further comprises a sample stage that positions said specimen such that said location corresponds to a plurality of different locations on said specimen.

7. The apparatus of claim 1 wherein said linear polarization filter comprises a polarization dependent beam splitter that splits light incident thereon into first and second analyzer beams, and wherein said apparatus further comprises a second detector, said first detector measuring an intensity of light in said first analyzer beam and second detector measuring an intensity of light in said second analyzer beam.

8. The apparatus of claim 1 wherein said MIR light source is frequency modulated.

9. The apparatus of claim 8 wherein said polarization axis is continuously rotated at a rotation frequency, and wherein said controller measures an average intensity from said first detector and an amplitude as a function of a frequency that depends on said rotation frequency.

10. The apparatus of claim 9 wherein said controller determines an intensity of diffusely reflected light and an intensity of specularly reflected light from said average intensity and said amplitude.

11. The apparatus of claim 1 wherein said controller determines an intensity of light corresponding to the intensity of diffusely reflected light from said location and the intensity of specularly reflected light having one polarization from said measured output from said first detector.

12. The apparatus of claim 1 wherein said illumination light beam is characterized by a wavelength and wherein said controller causes said MIR light source to output light of a second wavelength and wherein said controller measures said output of said first detector for each of said polarization axis positions for said second wavelength.

13. The apparatus of claim 1 wherein said controller varies said polarization axis by rotating said linear polarization filter about an axis defined in relation to said location.

14. The apparatus of claim 1 wherein said controller varies said polarization axis by rotating said specimen about an axis through said location.

15. The apparatus of claim 1 wherein said illumination beam is characterized by an illumination polarization direction and wherein said controller varies said polarization axis direction by varying said illumination polarization direction.

16. The apparatus of claim 1 further comprising a focal plane array of detectors, said light collection system imaging light from different locations on said specimen to different detectors in said focal plane array of detectors, said first detector being one of said focal plane array of detectors.

17. A method for generating a reflection spectrum from a sample, said method comprising a one wavelength method, said one wavelength method comprising:

illuminating said sample with a beam of linearly polarized light characterized by a measurement wavelength, and a source polarization direction;

filtering light reflected by said sample with a linear polarization filter characterized by a polarization axis that defines a direction of polarization of linearly polarized light that is reflected by said linear polarization filter;

measuring the intensity of light leaving said linear polarization filter for each of a plurality of different polarization axis positions; and determining an intensity of diffusely reflected light from said measured intensities.

18. The method of claim 17 further comprising determining an intensity of specularly reflected light from said measured intensities.

19. The method of claim 17 wherein said source polarization direction is maintained in a fixed relationship with said polarization axis direction.

20. The method of claim 17 further comprising repeating said one wavelength method for a plurality of different measurement wavelengths.

* * * * *

UNITED STATES PATENT AND TRADEMARK OFFICE
CERTIFICATE OF CORRECTION

PATENT NO. : 9,546,905 B1
APPLICATION NO. : 14/683841
DATED : January 17, 2017
INVENTOR(S) : Yang Han et al.

Page 1 of 1

It is certified that error appears in the above-identified patent and that said Letters Patent is hereby corrected as shown below:

In the Specification

In Column 10, Line 6, delete "$\Psi=2\theta_0+$" and insert -- $\Psi=2\theta_0+\delta$ --, therefor.

In Column 11, Line 19, delete "$D_2(\theta) = \frac{1}{4}((r^2)$" and insert -- $D_2(\theta) = \frac{1}{4}(r_s^2$ --, therefor.

Signed and Sealed this
Eighteenth Day of April, 2017

Michelle K. Lee
*Director of the United States Patent and Trademark Office*